United States Patent
Subbiah

(10) Patent No.: US 7,226,625 B2
(45) Date of Patent: Jun. 5, 2007

(54) IDENTIFICATION OF COMPOSITIONS, COMPOSITIONS, AND METHODS OF TREATMENT OF OBESITY AND OVERWEIGHT CONDITIONS

(75) Inventor: Ven Subbiah, Greenville, NC (US)

(73) Assignee: Phytomyco Research Corporation, Greenville, NC (US)

( * ) Notice: Subject to any disclaimer, the term of this patent is extended or adjusted under 35 U.S.C. 154(b) by 276 days.

(21) Appl. No.: 10/885,354

(22) Filed: Jul. 6, 2004

(65) Prior Publication Data

US 2005/0008718 A1 Jan. 13, 2005

Related U.S. Application Data

(60) Provisional application No. 60/485,808, filed on Jul. 9, 2003.

(51) Int. Cl.
*A61K 36/537* (2006.01)
(52) U.S. Cl. ............................ 424/746; 514/8; 549/299
(58) Field of Classification Search ...................... None
See application file for complete search history.

(56) References Cited

U.S. PATENT DOCUMENTS 4,917,913 A * 4/1990 Buckholz, Jr. et al. ..... 426/536

* cited by examiner

*Primary Examiner*—Susan Hoffman
(74) *Attorney, Agent, or Firm*—A. Jose Cortina; Daniels Daniels & Verdonik, PA

(57) ABSTRACT

A method for the identification of a composition useful in the treatment of an overweight or obese person to reduce the person's body mass index is provided which comprises obtaining an extract of an ethnobotanical plant, and evaluating the activity of the extract in an assay selected from the group consisting of a lipolysis assay, an assay that measures the amount of glycerol introduced by a cell into a suspension medium of the cell, an adipocyte differentiation assay, an assay that measures the level of the enzyme glycerol-3-phosphate dehydrogenase, an assay that measures the inhibition of differentiation of preadipocytes to adipocytes, an assay that measures the accumulation of lipid in an adipocyte, an assay that measures the de-differentiation of adipocytes into preadipocytes, and combinations thereof. Sclareol and sclareol-like compounds and sclareolide and sclareolide-like compounds are identified as useful in the treatment of overweight and obese conditions and disorders and conditions associated with adipose tissue abnormalities. These compounds can be formulated for oral administration.

7 Claims, 8 Drawing Sheets

Figure 4

Leptin procedure in flowchart form

Tissue Culture

1. Seed $2.5 \times 10^4$ 3T3-L1 cells per well in a 48-well plate

2. After cell become confluent (2-3 days), differentiate 3T3-L1 pre-adipocytes into mature adipocytes over the course of 12-15 days 3. Rest cells - Replace cell media with 150 ul of Basal media (serum free DMEM with 1% BSA) for 3 days.

4. Add samples and controls (1 or 10 ug/well) to wells. Positive control is

5. Collect cell supernatant after 3 days, centrifuge and take 50 ul of supernatant for analysis using Leptin ELISA kit using protocol suggested by manufacturer (R&D Systems cat#MOB00).

PPC 1=Sclareol; PPC 2=Sclareolide

IDENTIFICATION OF COMPOSITIONS, COMPOSITIONS, AND METHODS OF TREATMENT OF OBESITY AND OVERWEIGHT CONDITIONS

CROSS REFERENCE TO RELATED APPLICATIONS

This application is related to and claims priority to Provisional Application Ser. No. 60/485,808, filed Jul. 9, 2003, the disclosure of which is incorporated in its entirety by reference herein.

FIELD OF THE INVENTION

This invention relates to dietary supplement compositions and methods of administering such compositions to treat obesity. More particularly the invention relates to compositions and methods useful for reducing the rate of weight gain in an overweight and/or obese person, to compositions and methods for effecting weight loss in an overweight and/or obese person, to compositions and methods useful to reduce the body mass index of an overweight and/or obese person or animal, to compositions and methods useful for reduction and control of weight in the treatment of persons who are overweight or obese, and to methods of discovering compounds and compositions useful in the treatment of obesity and/or useful in producing a reduction in body mass index of an overweight or obese person. The invention relates to the field of dietary supplement compositions derived as extracts from ethnopharmacological plants, to methods useful to identify compounds in such extracts that are active in the treatment of obesity and overweight conditions, and especially to compositions comprising sclareol and/or sclareolide and their use in the treatment of overweight and obese persons, such as by oral administration.

BACKGROUND OF THE INVENTION

Body Mass Index (BMI) has been recognized by the U.S. Department of Health as a reference relationship between a person's height and weight. To determine a person's Body Mass Index in $kg/m^2$, the weight of the person, for example in pounds, is first multiplied by a conversion factor of 703 (with units of $kilogram.inch^2.pound^{-1}.meter^{-2}$), and that result is then divided by the height of the person, in inches squared. Alternatively, when height is measured in meters (1 inch=0.0254 meters) and weight in kilograms (1 pound Avoirdupois (U.S.)=0.4536 kg), the conversion factor is unity, and the Body Mass Index is obtained directly in units of $kg/m^2$.

Body Mass Index (BMI) can be used to determine when extra weight above an average or normal weight range for a person of a given height can translate into and signal increased probability for additional health risks for that person. Such health risks are considered to be related to the presence of additional weight above a desired range for that person.

Body Mass Index does not directly measure percent of body fat, although higher BMI's are usually associated with an increase in body fat, and thus excess weight. A BMI of 24 $kg/m^2$ or less is a commonly accepted guideline used to define a person with a healthy weight and who is neither overweight or obese. A desired BMI range is from about 18 $kg/m^2$ to about 24 $kg/m^2$, wherein a person is considered to have a healthful weight for the person's height. A Body Mass Index reading under 20 $kg/m^2$, and especially under 18 $kg/m^2$, is frequently considered to signify that the person is underweight which can be unhealthy. A person with a BMI above 24 $kg/m^2$, such as from about 25 $kg/m^2$ to about 30 $kg/m^2$, is frequently considered to be overweight, and a person with a BMI above about 35 $kg/m^2$ is frequently considered to be obese In another aspect, an individual who has a BMI in the range of about 25 $kg/m^2$ to about 35 $kg/m^2$, and has a waist size of over 40 inches for a man and over 35 inches for a woman, is considered to be at especially high risk for health problems.

Health risks related to a person being overweight and health risks related to a person being obese represent rapidly growing threats to the health of populations in an increasing number of countries worldwide. Obesity is a disease that is prevalent in both developing and developed countries and that affects children and adults alike.

Information available from the American Heart Association related to statistical results of the Third National Health and Nutrition Examination Survey 1988–1994 suggests that among American children aged 6 to 11 years, the following percentages were overweight, using 95th percentile of body mass index (BMI) values: for non-Hispanic whites, 10.3 percent of boys and 9.2 percent of girls were overweight; for non-Hispanic blacks, 11.9 percent of boys and 16.4 percent of girls were overweight; and for Mexican Americans, 17.4 percent of boys and 14.3 percent of girls were overweight.

Among adolescents aged 12 to 17 years, the following percentages were overweight, using the 95th percentile of BMI values: for non-Hispanic whites, 11.1 percent of boys and 8.5 percent of girls were overweight; for non-Hispanic blacks, 10.7 percent of boys and 15.7 percent of girls were overweight; and for Mexican Americans, 14.6 percent of boys and 13.7 percent of girls were overweight.

Among adults aged 18 and older, the following people are overweight (defined as a body mass index (BMI) of 25 $kg/m^2$ or higher): for non-Hispanic whites, over 62 percent of men and over 43 percent of women are overweight; for non-Hispanic blacks, over 64 percent of men and over 64 percent for women are overweight; for Hispanics, over 64 percent of men and over 56 percent of women are overweight; for non-Hispanic Asian/Pacific Islanders, over 35 percent of men and over 25 percent of women are overweight.

Among Americans aged 18 years and older, the median percentages of obesity are (defined as a body mass index or BMI greater than 30 $kg/m^2$): for whites, about 15 percent; for blacks, about 26 percent; for Hispanics, about 18 percent; for Asian/Pacific Islanders, about 4.8 percent; and for American Indians/Alaska Natives, about 30 percent.

Among Americans aged 20 to 74 years, an age-adjusted prevalence of being overweight (i.e., having a BMI of 25.0 $kg/m^2$ or higher) and of being obese (i.e., having a BMI of 30.0 $kg/m^2$ or higher) are: for non-Hispanic whites, about 61 percent of men and about 47 percent of women are overweight, and about 21 percent of men and about 23 percent of women are obese; for non-Hispanic blacks, about 58 percent of men and about 68 percent of women are overweight, and about 21 percent of men and about 38 percent of women are obese; for Mexican Americans, about 69 percent of both men and women are overweight, and about 25 percent of men and about 36 percent of women are obese.

Among American Indians aged 45 to 74 years, about 26 percent of men and about 31 percent of women are overweight (defined as a BMI of about 28 $kg/m^2$ to about 31 $kg/m^2$ for men and about 27 $kg/m^2$ to about 32 $kg/m^2$ for women), and about 35 percent of American Indian men and about 41 percent of women are obese (defined as a BMI of about 31 kg/m² or higher for men and a bout 32 kg/m² or higher for women).

The year-to-year rate of increase in the number of overweight children and adolescents is about 2 to 3 percent. Each year an estimated 300,000 U.S. adults die of causes related to the health risk of obesity. Over 100 million American adults (over 56 million men and over 52 million women) are overweight with a BMI of about 25 kg/m² and higher. Of these, over 44 million American adults (over 18 million men and over 25 million women) are obese, having a body mass index (BMI) of about 30 kg/m² or higher. (Obesity Clinical Guidelines: NIH Statement Jun. 3, 1998, press release).

A person can be overweight but not obese if that person's BMI is between about 25 to 30 kg/m², while a person who is obese with a BMI above 30 kg/m² is also overweight.

In one aspect, in order to lessen the risk for health problems in an overweight person and to improve that person's health, it is desirable to provide compositions and methods useful in the treatment of an overweight person which produces a reduction in the person's body mass index (BMI), preferably from a level above 25 kg/m² to a level below 25 kg/m², and more preferably to a BMI level between 25 kg/m² and 18 kg/m².

In another aspect, in order to lessen the risk for health problems in an obese person and to improve that person's health, it is desirable to provide compositions and methods useful in the treatment of an obese person which produce a reduction in the person's body mass index (BMI), preferably from a level above 30 kg/m² to a level below 30 kg/m², more preferably to a level below 25 kg/m², and most preferably to a BMI level between 25 kg/m² and 18 kg/m².

A person who has a BMI of between about 30 kg/m² to about 25 kg/m² is considered to be overweight, and a person who has a BMI of greater than about 30 kg/m² is considered to be clinically obese. Both genetic and environmental factors can contribute to a person becoming overweight or obese. The most common cause of weight gain that can produce elevations in a person's BMI that are synonymous to being overweight and/or obese is a high caloric food intake especially in the absence of exercise or physical activity. The resulting accumulation of surplus fat places overweight or obese individuals at increased risk of illness such as hypertension, lipid disorders, type 2 diabetes, cardiovascular diseases, high blood pressure, elevated levels of cholesterol, hyperlipidemia, coronary heart disease, stroke, gallbladder disease, osteoarthritis, joint pain, sexual and fertility problems, sleep apnea and respiratory problems, skin conditions, certain type of cancers, and a wide variety of other diseases and undesired physiological conditions, as well as overall mortality. An obese individual with a BMI above about 30 kg/m² is up to about fourteen times more likely to die at a significantly younger age than a lean person with a BMI below 25 kg/m². Obesity creates a high-risk medical burden on society and its treatment would be highly desirable. Eliminating or reducing obesity would also decrease medical costs for treating many co-morbid conditions.

The biochemical mechanisms related to adipogenesis, to becoming overweight and to becoming obese are complex and comprise a number of interactions between ligands and their receptors, such as leptin, NPY monoamines (dopamine, serotonin, and norepinephrine), and CART (i.e., cocaine amphetamine regulated transcript), and others.

The obesity phenotype is probably connected to over 250 genes, markers and chromosomal regions in the human genome. Commonly used markers for adipocyte differentiation include aP2 (fatty acid binding protein), GPDH (glycerol-3-phosphate dehydrogenase), and adipsin. Regulatory factors that influence adipogenesis by influencing transcription include the CAAT enhancer-binding proteins a, b, d (C/EBP a, -b, -d), peroxisome proliferator-activated receptors (e.g., PPARgamma), sterol response element binding proteins (SREBP), and preadipocyte factor 1 (pref-1). The progression of adipocyte differentiation can be characterized by a number of genetic changes involving expression of early, intermediate, and late genes.

Adipogenesis is a multistep organogenenic process that begins in the prenatal period, but unlike osteogenesis and myogenesis, the adipogenesis process never ends. In this process, mesenchymal cells can proliferate in clonal expansion, and at some point, some of these cells can differentiate into preadipocytes or cells committed to fill with lipid (i.e., fat) and then become adipocytes. When preadipocytes undergo a differentiation step and begin to fill with lipid, lipid first accumulates within the cell in small droplets (multilocular cells) and eventually the droplets fuse into one large droplet (unilocular cells). The adipocyte can continue to enlarge by accumulating additional lipid. A typical mesenchymal cell is 10 to 20 µm in diameter, but adipocytes can easily reach 100 µm (and in some cases 200 µm) in diameter. The volume of the cell can increase as much as a thousand fold largely because of lipid accumulation.

Obesity is the result of numerous, interacting behavioral, physiological, and biochemical factors. One increasingly important factor is the generation of additional fat cells, or adipocytes, in response to excess feeding or intake of food, especially food high in fat or comprising fat or fat pre-metabolites, and/or large increases in body fat composition. The generation of new adipocytes is controlled by several adipocyte-specific transcription factors that regulate preadipocyte proliferation and adipogenesis. Generally these adipocyte-specific factors are expressed following the induction of adipogenesis.

Reusch et al. in Mol Cell Biol. 2000 February; 20 (3): 1008–1020 noted that transcription factor(s) involved in initiating adipocyte differentiation had not been identified, but described how the transcription factor, CREB, was constitutively expressed in preadipocytes and throughout the differentiation process. They noted that CREB was stimulated by conventional differentiation-inducing agents such as insulin, dexamethasone, and dibutyryl cAMP. Stably transfected 3T3-L1 preadipocytes (L1 cells) were generated in which they could induce the expression of either a constitutively active CREB (VP16-CREB) or a dominant-negative CREB (KCREB). Inducible expression of VP 16-CREB alone was sufficient to initiate adipogenesis as determined by triacylglycerol storage, cell morphology, and the expression of two adipocyte marker genes, peroxisome proliferator activated receptor gamma 2, and fatty acid binding protein. KCREB alone blocked adipogenesis in cells treated with conventional differentiation-inducing agents. These data suggested that activation of CREB was necessary and sufficient to induce adipogenesis. CREB was shown to bind to putative CRE sequences in the promoters of several adipocyte-specific genes. These data also suggested CREB as a primary regulator of adipogenesis.

Insulin can play a role in controlling adipogenesis. Several factors exert positive and negative influences on the process of adipogenesis. When insulin binds to its receptor it causes a signal cascade that ultimately leads to the translocatation of GLUT-4 receptors to cell surface membranes to allow glucose to be taken up by the cells.

Understanding weight regulation involves, in part, unraveling the roles played by insulin and leptin in regulating appetite control and energy expenditure in the brain. Both of these blood-borne signals provide information to the brain about fat storage. Homeostasis and glucose metabolism is ultimately regulated in the hypothalamus, specifically in the arcuate nucleus (ARC) region. Two subsets of neurons in the ARC express receptors for insulin and leptin and are believed to effect metabolism through an anabolic/catabolic regulation pathway. The proposed catabolic circuit involves the proopiomelanocortin (POMC) expressing neurons. These are activated by insulin and leptin causing the release of the neuropeptide α-MSH, believed to increase energy expenditure and reduce food intake. Neuropeptide Y (NPY) and agouti related protein (AgRP) expressing neurons complete the anabolic circuit becoming activated by low levels of insulin and leptin, stimulating downstream neurons to increase food intake and energy storage (i.e., increase insulin levels). Insulin and leptin satisfy criteria required for adiposity signals: secretion into plasma in proportion to body fat stores, transport into the brain from the bloodstream, expression of signal-transducing molecules in brain areas that control energy homeostasis, and the ability to reduce food intake upon central administration.

One potential cause of obesity is a resistance or desensitization of receptors to insulin and leptin in the blood, which results in an increase of food intake and body adiposity as well as glucose intolerance, hyperleptinemia, and reproductive abnormalities. Several factors can play a role in determining cell sensitivity to insulin.

Thiazolidinediones can increase insulin sensitivity, while several substances including tumor necrosis factor (TNF-α), growth hormone, plasminogen-activator inhibitor-1, angiotensin 2, free fatty acids, and the hormone resistin can decrease insulin sensitivity. Insulin can up-regulate resistin gene expression, possibly serving as a negative feedback loop, while isoproterenol, the cytokine TNF-α, and activation of β-adrenoceptors suppress resistin expression and secretion. TNF-α can act as a regulator of adipocytes, and may be involved in the development of Type II diabetes as well as obesity.

Available treatments for obesity can produce undesirable and serious side effects or such treatments may lack efficacy. Obesity and overweight conditions may become partially reversed or prevented by employing diet or nutrition and behavior modification programs or by administration of pharmaceutical therapeutic (drug) compositions. Widely administered drugs include orlistat, which reduces the amount of dietary fat that is absorbed from the intestine; sibutramine, which suppresses appetite by inhibiting the re-uptake of norepinephrine and serotonin; fenfluramine and d-fenfluramine, which suppress appetite by both releasing serotonin and then inhibiting its re-uptake; and phentermine, which suppresses the appetite by stimulating the release of norepinephrine.

Drug therapies for weight reduction usually achieve only a 5% to 10% decrease in body weight (National Task Force on the Prevention and Treatment of Obesity: Long-term pharmacotherapy in the Management of Obesity, JAMA 276:1907–15, 1996).

Many drugs produce mild to serious side effects in overweight and obese patients. Common side effects include dizziness, headaches, rapid pulse, palpitations, sleeplessness, hypertension, diarrhea, and intestinal cramping. The combination of fenfluramine and phentermine, which produced a 15% to 20% reduction in body weight (F. Brenot et al., Appetite Suppressant Drugs and the Risk of Primary Pulmonary Hypertension, N. Engl. J. Med., 335:609–16, 1996), also provided an increased the risk of heart valve damage and a number of confirmed patient deaths related to "Fen-Phen".

Medications used for weight loss can fall into two groups: those that reduce the absorption of nutrients into the body and those that reduce appetite and thereby decrease food intake.

Adipose tissue produces leptin that reaches homeostatic hypothalamic centers in the brain and provides information on the state of the energy balance. Adipocytes play a critical role in the storage of energy as lipid and in the overall regulation of the body's metabolism. That adipocytes are endocrine cells that have a profound effect on human physiology has been postulated for over 40 years. Recent studies indicate that obesity affects about 30% of the population and that obesity has been identified as a risk factor for metabolic diseases such as type 2 diabetes, hypertension, and hyperlimidia. A better understanding of human adipocyte biology is critical to the development of pharmacological agents to treat these devastating diseases.

Orlistat (branded as Xenical) was approved by the FDA for reducing nutrient absorption. Agonasts are known to induce lipolysis, and thereby have the potential to offer weight-lowering properties. Beta-agonists, such as isoproterenol and turbataline, have been shown to increase lipolysis, leading to an increase in energy expenditure and a decrease in fat stores. Beta-agonists can also modulate glucagon and insulin secretion, liver metabolism and glucose uptake in muscle via beta-adrenergic receptors (beta2adrenergic receptor, beta3adrenergic receptor). In addition, polymorphisms of the beta3adrenergic receptor may be involved in insulin resistance and hypoglycemeia. However, use of beta-agonist can also lead to hyperglycemia, or an increase in blood sugar levels as well as insulin desensitization.

A number of weight loss drugs have been marketed, but most have undesired side effects for the patient. For example, a combination of amphetamine and dextroamphetamine, branded as Adderall, is a sympathomimetic amine appetite suppressant with high abuse potential. Benzphetamine, branded as Didrex or Benzfetamine, is a sympathomimetic amine appetite suppressant also with high abuse potential. Bromocriptine, branded as Ergoset or Parlodel, stimulates dopamine type-2 receptors and antagonizes type-1 receptors in brain, but it is not approved for treatment of obesity although it is used off label. Dexfenfluramine, branded as Redux, acts as an appetite suppressant via serotonin release and serotonin reuptake block, but it was voluntarily withdrawn from the market because of evidence of heart valve damage. Dextroamphetamine, branded as Dexedrine, is a sympathomimetic amine appetite suppressant used off-label for obesity although it is highly abused. Diethylpropion, branded as Amfepramone and Tenuate, is a sympatho-mimetic amine appetite suppressant with a possible link to primary pulmonary hypertension. Fluoxetine, branded as Prozac, is a selective serotonin reuptake inhibitor (SSRI) that is used off-label. Mazindol, branded Mazanor and Sanorex, is a sympathomimetic amine appetite suppressant subject to high abuse potential. Methamphetamine, branded as Desoxyn or Methampex, is a sympathomimetic amine appetite suppressant subject to high abuse potential. Orlistat, branded as Xenical, is not a CNS-active drug but can decrease the amount of fat absorbed from the diet by about 30%. However, the drug may have a link to breast cancer. Other sympathomimetic amine appetite suppressants include Phendimetrazine, Phentermine which was approved as a resin complex, and Phenylpropanolamine which is available over the counter. Additionally, Sibutramine, branded as Meridia inhibits reuptake of dopamine, norepinephrine, and serotonin in the brain.

In addition to the above types of drug therapeutic agents, a number of herbal weight reduction formulas have also been suggested as alternatives to both prescription and over-the-counter weight loss compounds. Formulations containing herbal components can have fewer side effects than prescription and over-the-counter medications, but some herbal formulas can still be abused. For example, improper administration of herbal weight loss formulas based primarily on ma huang (ephedra) and high caffeine-containing herbs, such as guanrana and kola nut, may result in diminished energy and a depleted body.

U.S. Pat. No. 6,541,046 describes an herbal composition for hindering weight gain comprising: rhubarb, turmeric, astragalus root, red sage root, and ginger root.

U.S. Pat. No. 6,322,823 describes an aromatherapy composition directed to combat symptoms of premenstrual syndrome (PMS) comprising externally applied highly concentrated essential oils extracted from plant cells. The composition can comprise a mixture of essential oil of geranium, essential oil of clary sage, and essential oil of orange, and can be applied directly on the skin or in a carrier.

Given the prevalence and serious problems associated with obesity, and the significant drawbacks associated with many weight loss compounds, a need exists for a means to discover compounds and compositions that are safe and effective in the treatment of persons that are overweight or obese to reduce weight gain, cause weight loss, and reduce body mass index to acceptably healthy levels in the range of 25 to 18 kg/m$^2$.

BRIEF SUMMARY OF THE INVENTION

The present invention provides compositions (pharmaceutical, nutraceutical, or both), including compounds and formulations, and methods useful in the treatment of a wide variety of physiological and mental disorders and abnormal conditions, including those disorders and conditions related to being over a normal healthy weight for body height (over weight), body mass higher than normal and healthy body mass for a given height (high body mass), blood sugar levels higher than observed in a normal and healthy individual (high blood sugar), and cholesterol levels above the range observed in normal and healthy individuals (hypercholesterolemia or high cholesterol) in humans and animals. The compositions (extracts, mixtures, isolated compounds, and formulations of these) and methods of the present invention are useful in treating undesired or unhealthy conditions and/or disorders such as over weight and other metabolic diseases, such as high blood sugar, diabetes, hypertension, pulmonary hypertension, hyperlipidemia, hypercholesterolemia, hyperlipoproteinemia, and the like.

The use of plants, in particular, extracts of plants to treat obesity has been documented. For example, plants effective for such purposes are identified in natural product databases including but not limited to the NAPRALERT database and the Chapman Hall natural product database. In accordance with the invention, while many plants are identified for obesity treatment in such databases, it has been unexpectedly discovered that plants effective to induce lipolysis and/or increase leptin secretion are particularly effective. Thus, there is provided a method of identifying such plants, extracting and preparing compounds effective to induce lipolysis and/or increase leptin secretion. There is also provided a method of treating obesity by administering of such compounds.

In accordance with the invention, it has been discovered that sclareol and sclareol-like compounds and sclareolide and sclareolide-like compounds can be formulated and used in combination with a pharmaceutically and nutraceutically acceptable carrier, such as a carrier comprising a pharmaceutically acceptable excipient and/or diluent, to provide a pharmaceutical and/or nutraceutical composition suitable for use in treatment of a one or more diseases related to conditions or overweight and obesity. In one embodiment, sclareol-like and sclareolide-like compounds can be used in the treatment of obesity to achieve a reduction in body mass index in a patient, diabetes, hypercholesterolemia to achieve a lowering of cholesterol levels in the blood, and coronary heart disease. These compounds are shown to induce lipolysis and/or increase leptin secretion.

Accordingly, the present invention relates to a method of treating abnormal conditions and disorders such as over body weight disorders including obesity and related conditions. In one embodiment, a method of the invention comprises administering to a subject an active compound of the present invention (i.e., a sclareol-like and/or sclareolide-like compound) in an amount sufficient to treat the disorders such as to achieve a reduction in body mass index, a reduction in cholesterol level, a reduction in low density lipid levels, and the like. The compounds and compositions of the present invention may be provided to the subject in a pharmaceutical or nutraceutical formulation, examples of which formulations are also described herein as embodiments of the invention. Another embodiment of the invention involves a method of using a Sclareol-like and sclareolide-like compounds to treat or manage diabetes and/or to treat or manage coronary heart disease, particularly to treat or manage those disorders and conditions associated with adipose tissue abnormalities. Adipose tissue abnormalities.comprise risk factors directly related to metabolic abnormalities and diseases such as type 2 diabetes, hypertension, and hyperlipidemia.

There is a continuing demand for dietary supplements that are useful and effective in treatments to reduce body weight and body mass index from overweight and obese levels to less overweight and ultimately to normal levels. Compositions of this invention have been assessed for utility in treatment of overweight and obese conditions using cell-based assays that are useful for detecting weight-lowering substances.

BRIEF DESCRIPTION OF THE SEVERAL VIEWS OF THE DRAWING

FIG. 4 is a schematic representation of a commercially available ELISA assay that can be used to detect compounds that induce the release of leptin in this invention.

DETAILED DESCRIPTION OF THE INVENTION

Figure 1A:
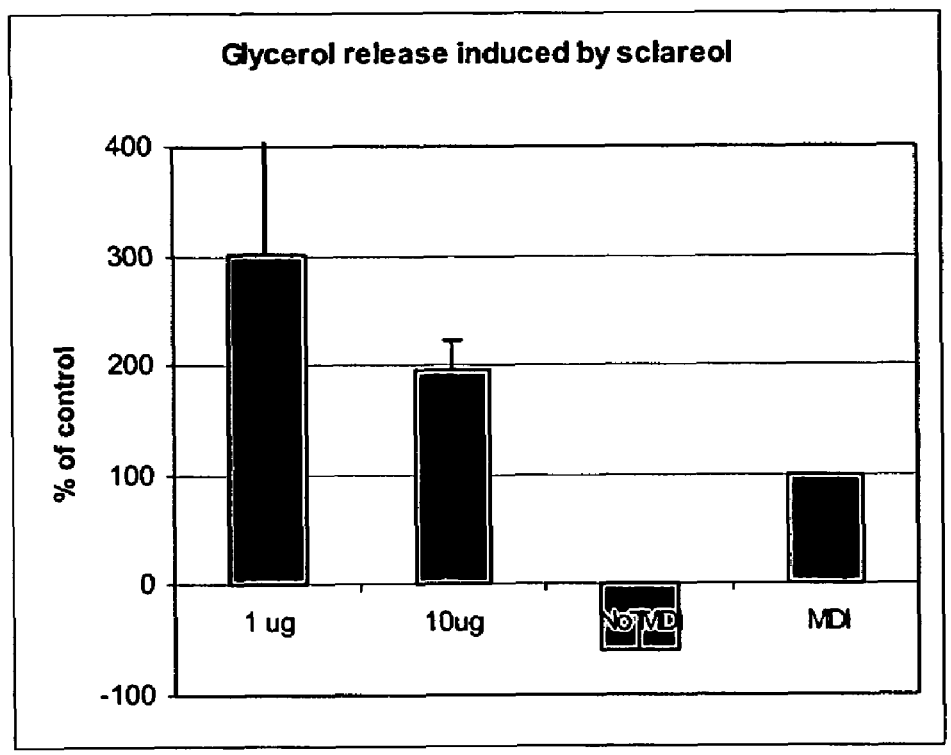
FIG. 1A shows the effect, as a percentage of the untreated control average, of sclareol on lipolysis via glycerol release in 12-day old differentiated adipocyte treated with 5 or 50 ug/ml of sclareol for 3 hours.

Specific agonists of CART (cocaine amphetamine regulated transcript) peptide receptors can be useful in treating obesity.

3T3-L1 cells (L1 cells), derived from mouse embryos, are preadipocytes and can be induced to morphologically change into adipocytes (fat cells), which are detectable microscopically by the presence of oil droplets in the cytoplasm. Cell-based assays which employ the 3T3-L1 cell line can provide an in vitro model useful to study adipocyte differentiation and obesity. Cell-based assays which employ the 3T3-L1 cell line can also provide an in vitro model useful to detect substances and compounds that have an effect on obesity or weight loss.

Compounds that block differentiation of preadipocytes to adipocytes (fat cells) can be useful in that they can prevent the development of cells whose function is the accumulation and/or synthesis of stored triacylglyceride or fat. Because an adipocyte secretes a number of inflammatory cytokines, blocking the differentiation process can also result in less need for inflammatory mediators such as TNF-α, whose presence is correlated with insulin resistance.

Myostatin, an adipocyte blocking agent, is an inhibitor of skeletal muscle growth and is secreted from muscle tissue. Like other members of the TGF-β superfamily, myostatin inhibits differentiation of preadipocytes in 3T3-L1 cells. A decrease in GPDH (glyceraldehyde phosphate dehydrogenase) activity as well as morphological evidence (e.g., oil red O staining) shows that myostatin inhibits adipogenesis. On the molecular level, myostatin did not alter C/EBPβ expression, but did cause a decrease in the expression of the downstream genes C/EBPα and PPARγ (Kim et al. 2001). Consequently, since C/EBPα activates the promoter for leptin, while PPARγ antagonizes activation of the promoter (He et al 1995), myostatin had no effect on leptin levels.

Several methods have been developed to detect the inhibition of adipocyte differentiation. Lipophilic dyes can be used to stain adipocytes such as Oil red O and Red Nile. Branched DNA (bDNA) analysis can be used to measure the niRNA levels in cells for adipocyte specific marker genes, such as AP2, a fatty acid binding protein specifically expressed in adipocytes. Its expression is controlled by the nuclear transcription factor peroxisome proliferator-activated receptor γ (herein referred to as PPARγ). PPARγ is predominately expressed in adipose tissue and along with the transcription factors C/EBP α, β and δ (from the CCAAT/enhancer binding protein family) play a role early in adipose differentiation by regulating the promoters for several adipogenic genes.

Enzymes that are upregulated in fat cells can be utilized as markers for adipocytes, such as glyceraldehyde phosphate dehydrogenase (GPDH).

Triglyceride synthesis and accumulation is one of the events that signals late stage adipocyte differentiation and therefore cell maturity. It is also at this stage in differentiation that adipocytes acquire insulin sensitivity. Triglyceride synthesis and accumulation in adipocytes relate the role played by adipocytes as endocrine cells and stores of energy. Compounds that induce lipolysis may be used to reduce the storage of fat in the body. Additionally, such compounds may break down existing lipids/fat cells; or at least lower the fat content of cells. The breakdown of triglyceride in adipocytes leads to secretion of free fatty acid and glycerol into the medium. Understanding what causes the breakdown of triglycerides in the cell could have a profound impact on the development of antiobesity drugs.

In this invention, in one embodiment, in one aspect a compound that can induce lipolysis can be used as an anti-obesity drug in the treatment of obesity to reduce the storage of fat in the body. In another aspect, a compound that can induce lipolysis can be used as an anti-obesity drug in the treatment of obesity to break down existing lipids in fat cells. In another aspect, a compound that can induce lipolysis can be used as an anti-obesity drug in the treatment of obesity to reduce the fat content of cells. The body mass index of a human or animal patient who is overweight can be reduced from the range between 30 kg/m$^2$ to 25 kg/m$^2$ to about 24 kg/m2 by a method of treatment comprising administration to the patient of a compound that can induce lipolysis in adipocytes of the patient. The body mass index of a human or animal patient who is obese can be reduced from the range above 30 kg/m$^2$ to a range between 30 kg/m$^2$ to 25 kg/m$^2$ and more preferably to about 24 kg/m2 by a method of treatment comprising administration to the patient of a compound that can induce lipolysis in adipocytes of the patient.

In this invention, in another embodiment, in one aspect a compound that can block differentiation of a cell into an adipocyte, for example a compound that can block the differentiation of a preadipocyte cell into an adipocyte, can be used as an anti-obesity drug and in the treatment of overweight conditions and obesity to reduce the storage of fat in the body. In another aspect, a compound that can block differentiation of a cell into an adipocyte can be used as an anti-obesity drug and in the treatment of overweight conditions and obesity to prevent cells from accumulating fats or lipids in adipocytes or fat cells. In another aspect, a compound that can block differentiation of a cell into an adipocyte can be used as an anti-obesity drug in the treatment of overweight conditions and in the treatment of obesity to reduce the fat content of cells. The body mass index of a human or animal patient who is overweight can be reduced from the range between 30 kg/m$^2$ to 25 kg/m$^2$ to about 24 kg/m2 by a method of treatment comprising administration to the patient of a compound that can block differentiation of a cell into an adipocyte of the patient. The body mass index of a human or animal patient who is obese can be reduced from the range above 30 kg/m$^2$ to a range between 30 kg/m$^2$ to 25 kg/m$^2$ and more preferably to about 24 kg/m$^2$ by a method of treatment comprising administration to the patient of a compound that can block differentiation of a cell into an adipocyte of the patient.

Compounds that block differentiation of cells to adipocytes (fat cells) would be useful in that they would prevent cells from accumulating fat/lipids. In effect, fat would not be stored when cells have all the energy they require.

A fruit from the genus *Garcinia* shows lipolytic activity in adipose tissue. In rat livers, garcinia extract can inhibit fatty acid synthesis and subsequent lipid accumulation. *Garcinia* extract is currently used as a dietary supplement in the health food industry.

Leptin, a product of the obese gene, is a hormone secreted by mature adipocytes that may play a role in regulating body fat stores, energy expenditure and food intake. Leptin expression is regulated by physiological states such as fasting and feeding and by hormonal regulation as well as cytokines like TGF-β.

Insulin-stimulated glucose metabolism also plays a role in regulating leptin secretion. Glucose metabolism induced by insulin, rather than insulin itself per se, can increase the transcriptional activity of a promotor for leptin in human adipocytes as well as human subjects. Compositions that induce similar or higher levels of leptin secretion compared to insulin-induced leptin secretion) could be potentially useful drugs clinically.

Obesity and diabetes are inter-related and operate through similar/overlapping mechanisms and pathways. Because of the complexity of these metabolic disorders (and the multiple cell signaling pathways involved in each), discovery of new compounds to treat these disorders can be difficult. In order for a unique compound/extract to be taken to animal studies, which are time consuming and expensive, and then through drug development stages, solid mechanism based evidence must be gathered. Since there are multiple mechanisms/pathways involved in the onset of diabetes and obesity, a single assay/approach may be limiting for discovery of new chemical entities. Additionally the mechanism can be unknown. Therefore, we have taken a novel approach to this problem. I have developed a battery of assays to be used to quantify the ability of a test compound or extract of a plant to affect a mechanism related to the production or maintenance of obesity and potentially also of diabetes.

I have discovered that novel dietary supplements can be used for the treatment of disorders of fat tissue such as obesity and diabetes. Obesity can be treated effectively and safely at the level of the fat cell, rather than indirectly by modulating central nervous system (CNS). With this approach, selective agents can be identified for use in the treatment of disorders of fat tissue such as obesity and diabetes, which agents do not exhibit CNS or cardiovascular side effects. I have developed unique, cellular, HTP-screening assays using the culture of mouse adipocytes and preadipocytes to identify agents that are useful in the treatment of obesity. These assays allow one skilled in the art to focus on the detection of potential botanicals which target human fat tissue. These assays are primary cellular screens and follow-up response screens and engineered cellular screens. These assays can be used at an early stage in a drug discovery process with a strategy to maximize screening capacity to identify relevant products that are usefull in the treatment of overweight conditions and obesity, and which are useful to lower the BMI index of an overweight or obese person toward and to the level of a healthy individual with a BMI index of 24 kg/m$^2$.

An array of cell-based assays has been developed and validated to detect and discover novel compounds and compositions (referred to as weight loss compounds) that exhibit activity in the treatment of overweight and obese conditions and which, when administered to a patient in need of treatment, result in weight loss in an overweight or obese person. It is an advantage of this invention that these weight loss compounds and compositions can be easily and readily identified by their relative activities against reference assay results and against results of assays employing a reference compound of known activity employing these assays in order to rapidly screen fractions of plants for new sources of safe and effective herbal ingredients. It is another advantage of this invention that active compounds are discovered in the extracts of plants. In addition, it is an advantage of this invention that rather than randomly searching a compound library, I have focused my screening assays toward plant extracts to discover individual compounds and mixtures that are derived from plants which have been associated with ethnobotanical information and a history of safe usage. It is another advantage of this invention that assays have been identified to permit the evaluation of candidate plants with maximum efficiency, greatly reducing research and development time and expense.

Extracts from ethnobotanical plants can be conveniently chemically modified, for example, such as by treatment with acylating reagents such as organic acid halides or anhydrides or active esters to provide acylated extracts that can be screened in the assays to identify additional compounds that are useful in this invention. Additional methods of chemical modification of extracts include hydrogenation of some or all of olefinic groups in extracts, oxidation of alcohols, esterification by peroxidation, epoxide formation, ozonolysis, nitration, sulfmation, sulfonation, sulfate formation, and phosphorylation.

Figure 3:
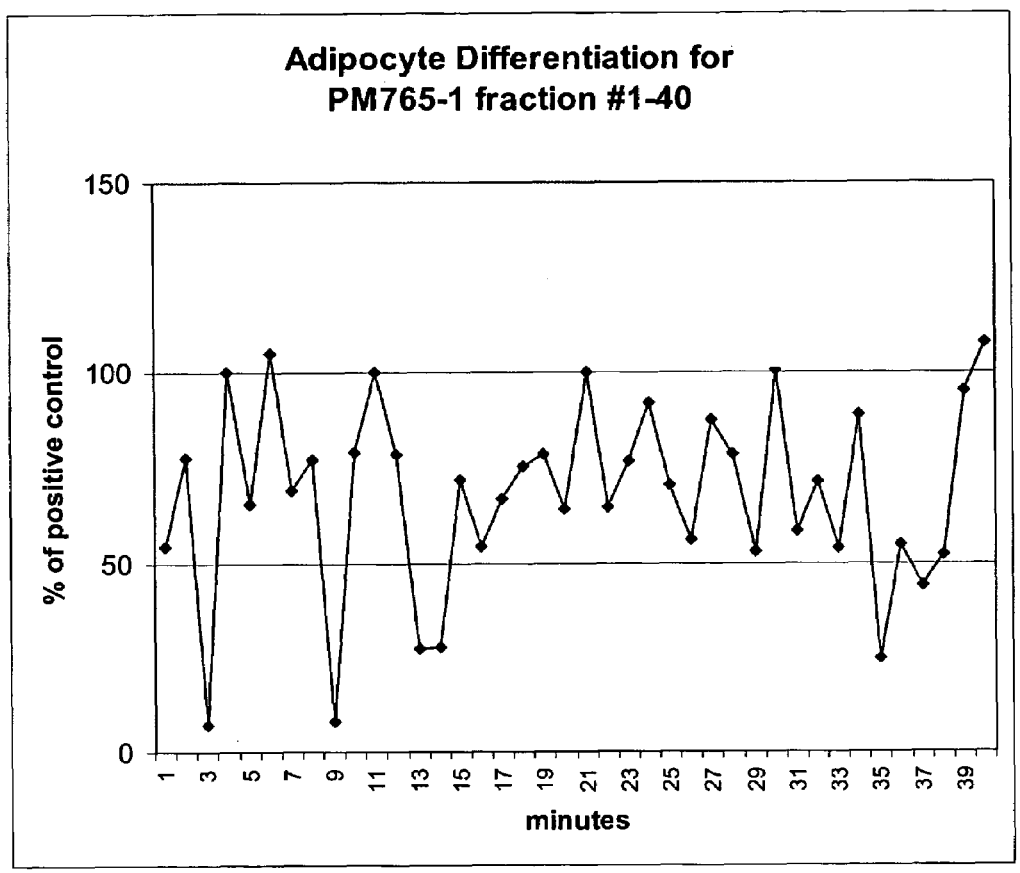
FIG. 3 is a fractionation by HPLC of fractions isolated collected at 30 second or 1 minute HPLC eluant flow time intervals of two plant extracts designated as PM765 and as PM902 that are active in the adipocyte differentiation blocking assay herein. The collected HPLC eluant fractions are divided into 40 or 120 fractions in collection wells.

The adipocyte differentiation blocking assay is an enzyme assay that examines the ability of compounds to block differentiation of preadipocytes to adipocytes by quantifying the level of GPDH in cell lysates (inhibition of adipogenesis). Based on preliminary results using this assay, we selected two plant extracts (designated as PM765, and as PM902, respectively) and collected eluant fractions isolated by HPLC, the extracts being divided into 40 or 120 fractions in collection wells (collected at 30 second or 1 minute HPLC eluant flow time intervals) (FIG. 3). The cellular differentiation assay results indicate adiopogenesis blocking activity to be present in those fractions (or wells) that contained cells that did not differentiate into adipocytes after being exposed to a standard MDI treatment. MDI treatment is defined as Differentiation media causes the 3T3-L1 preadipocytes (fibroblast cells) to differentiate into adipocytes (fat cells). Differentiation media is composed of:

Per 100 ml of differentiation media
90 mL DMEM media
10 mL FCS
1% pen/strep
1 ml methylisobutylxanthine (stock 11.5 mg/mL)
100 ul dexamethasone (stock 0.4 mg/mL)
1 ml insulin (stock 1 mg/mL)

The marker compound in these samples can be identified for additional assay guided fractionation.

In addition, we also screen for substances that will cause adipocytes to revert their phenotype back to preadipocytes, that is, we also screen for substances that will cause adipocyte de-differentiation, by assessing the GPDH enzyme levels in treated cells. Multiple treatments with TNF-α cause dedifferentiation of adipocytes. A commercially available ELISA kit can be used to detect compounds that induce the release of leptin (FIG. 4)). And fully, to assess the effects of our plant extracts on lipolysis, an assay dubbed GPO Trinder assay available from Sigma-AldrichChemical Company is used. This assay detects glycerol released into a cell medium as a result of triglyceride (fat) breakdown.

We have found that active compounds of the present invention include sclareol and sclareol-like compounds. Sclareol-like compounds are diterpene compounds, and include, for example, sclareol, 13-episclareol, ferruginol, salvipisone, aethopisome, neoclerodane, sagequinone, romulogarzone, ortho-benzoquinone, para-benzoquinone, and clariol. Other sclareol-like compounds include abietane and icetexane diterpenoids, languidulane diterpene, paryin and pimarine diterpenes, methylene quinone diterpenoids, manoyl norditerpenoids, multicaulin, salvipimarone and pimarane diterpenoid. Additional examples of sclareol-like compounds that can be useful in this invention can be found, for example, in Gonzalez et al., Can. J. Chem. 67(2), 208–212(1989); Eanthorpe et al., Phytochem. 29, 2145–2148(1990); Kouzi et al., Helv. Chim. Acta. 73(8), 2157–2164 1990); Abraham, Phytochem. 36(6) 1421–1424 (1994); Ulubelen et al. Phytochem. 36(4), 971–974 (1994); Hanson, Nat. Prod. Rep., 13, 59–71 (1996) and Topcu et al., J. Nat. Prod. 59, 734–737 (1996).

We have found that active compounds of the present invention also include sclareolide and sclareolide-like compounds. Sclareolide-like compounds are fused-ring diterpene compounds that may be derived from sclareol by chemical or biological techniques known to those skilled in the art; and include, for example, sclareolide, ambrox, and wiedenol. Additional examples of sclareolide-like compounds that can be useful in this invention can be found, for example, in Hanson, Nat. Prod. Rep. 13, 59–71 (1996); Chackalamanni et al., Tetrahedron Letters 36, 5315–5318 (1995); Barrero et al., Tetrahedron Letters 35, 2945–2948 (1994); Martres et al. Tetrahedron Letters 34, 801–8084 (1993) and Barrero et al., Tetrahedron 49(5), 10405–10412 (1993).

Preferred compounds in this invention are found in the extracts obtained from ethnobiological plants.

The active compounds of this invention typically are cosmetically or pharmaceutically acceptable analogs, derivatives, or salts of sclareol or sclareolide. In the practice of the present invention, the active compounds may alternatively be substituted with alkyl (both unsaturated and saturated, and branched and unbranched, such as methyl, ethyl, or isopropyl), aryl, halogen, hydroxy, alkoxy, and amino groups, as will be apparent to those skilled in the art. Additionally, any of the active compounds of the present invention may be present as an optical isomer, or chiral compound, or as a mixture of optical isomers and chiral compounds. These isomers may be isolated in pure form or enriched, for example, as a 50:50 racemic mixture of two isomers enriched to up to 100% of one isomeric pure form. Individual isomers or mixtures of isomers can be useful in this invention. The net activities of a mixture of one or more isomers will be observed in the assays of this invention.

Sclareol is an important bioactive diterpene obtained from clary sage (*Salvia sclarea* L.). This diterpene is not widely distributed and the most convenient sources are flower heads of clary sage plant.

Sclareol is obtained by solvent extraction of clary sage. U.S. Pat. No. 3,060,172 describes a process for the isolation of sclareol from clary sage. U.S. patent application Ser. No. 08/92,081, filed Jan. 31, 1997, and 08/824,147, filed Mar. 25, 1997, which applications are incorporated herein in their entirety by reference, describe additional methods of isolation of sclareol.

Sclareolide is prepared by either chemical oxidation followed by lactonization of sclareol or by biotransformation of sclareol using a yeast strain. Exemplary methods of producing sclareolide include those methods disclosed in U.S. Pat. No. 5,525,728 (to Schneider et al.), U.S. Pat. No. 5,247,100 (to Gerke et al.), and German Patent Application DE 3942358 (to Gerke et al). Briefly, these processes use a ruthenium catalyst and an oxidation step to convert sclareol into sclareolide that is present in a crude reaction product. Other exemplary methods of converting sclareol to sclareolide include the biotransformation and fermentation methods described in U.S. Pat. Nos. 4,970,163 and 5,212,078, both to Farbood et al. Sclareolide produced by these described methods is normally provided in wet or dry cake form, and is generally from about 90% to 95% pure. Sclareolide has also been reported to have therapeutic properties. See, PCT Application No. WO 06/00704 to Braquet et al. The disclosures of these patents setting forth methods of producing sclareolide from sclareol are incorporated herein by reference in their entirety.

Sclareol is a labdane diterpene (labdane-14-ene-8,13-diol) used in the fragrance industry in perfume manufacture, and also to enhance the flavor of tobacco (U.S. Pat. No. 4,441,514). Sclareol diol is chemically named decahydro-2-hydroxy-2,5,5,8a-tetramethyl-1-naphthaleneethanol. The compound is found in nature in many plant sources including *Acacia* sp. (Fonster et al., Phytochemistry 24:2991–1993, 1985), *Salvia palestina* (Phytochemistry 24:1386–1387, 1985) *Stevia monardaefolia* (Phytochemistry 21:2369–1371, 1982), *Nicotiana glutinosa* (Bailey et al. J. Gen. Microbiol. 85:57–84, 1974), and *Salvia sclarea* (U.S. Pat. No. 3,060,172). The latter species, also known as clary sage, represents a primary commercial source of sclareol. The sclareol produced by *S. sclarea* occurs in the flower stalks in the epidermal appendages or hairs known as trichomes. Although the concentration of sclareol in these hairs is relatively high, it is the primary location on the plant where sclareol is produced; there is little or no sclareol present in the leaf, root or stems of clary sage.

U.S. Pat. No. 2,905,575 describes the use of alpha-hydroxy-2,5,5,8a-tetramethyl-1-naphthaleneethanol (sclareol diol) in tobacco to impart a cedar-like aroma to the mainstream smoke.

U.S. Pat. No. 5,906,993 describes a method for treating a disorder characterized by excessive cell proliferation in a patient by administering to the patient a therapeutically effective amount of sclareolide. It also describes a method of treating excessive proliferation of benign and malignant cells in mammals comprising administering an amount of (+) sclareolide sufficient to reduce proliferation of benign and malignant cells.

(+) Sclareolide is 3aR-[3a-alpha, 5a-beta, 9a-alpha, 9b-alpha]-decahydro-3a,6,6,9a-tetramethylnaphtho[2,1-b]furane-2(1H)-one, and is a natural bicyclic terpenoid which is found for example in tobacco (Kaneko, Agr. Biol. Chem. 35(9): 1461 (1971)).

(+) Sclareolide is known for increasing or developing the organoleptic properties of food products as described in U.S. Pat. Nos. 4,917,913; 4,960,603; 4,966,783; 4,988,527; and 4,999,207. (+) Sclareolide has been used as a perfume for cigarettes (Japanese Patent 60,123,483) and as an additive to eliminate the bitter taste of coffee (U.S. Pat. No. 4,988,532). (+) Sclareolide is available from a specific number of commercial sources, for example Aldrich Chemical Co., St. Louis, Mo. (+) Sclareolide may also be prepared by synthesis, for example from (–) sclareol (Aldrich Chemical Co.) or homophamesylic acid. See for example Coste Maniere et al., Tetrahedron Letters, 29(9):1017 (1988), Mantres et al., Tetrahedron Letters 34(4):629 (1993); German Patents No. DE 4,301,555 and DE 3,942,358 and PCT Application No. WO 93/21,174.

Subbiah, in U.S. Pat. No. 6,331,551 and in U.S. Pat. No. 6,150,381, the disclosure of each of which is herein incorporated by reference, describes a cosmetic formulation for treating a skin disorder caused by a microbial infection, comprising a sclareol-like or a sclareolide-like compound in an amount sufficient to treat said skin disorder, in a cosmetically acceptable carrier, and a method of treating a skin disorder such as acne caused by a microbial infection, comprising administering a compound selected from the group consisting of sclareol and sclareolide to said subject in an amount effective to treat the disorder, wherein the microbe causing the microbial infection is a bacterium from the group consisting of *Propionibacterium acnes, Enterobacter aerogens,* and *Bacillus subtilis.*

Subbiah, in U.S. Pat. No. 5,945,546, the disclosure of which is incorporated in its entirety herein by reference, describes a method for purifying sclareolide which comprises a separation step wherein microbial cell debris is removed, and further comprises extracting an organic solution of sclareolide with an acid solution, followed by an extraction of the partially purified sclareolide with a basic solution, thus yielding sclareolide of very high purity.

U.S. Pat. No. 5,012,040 describes a somaclonal variant *Nicotiana glutinosa* plant and derivatives thereof which produces at least about 800 milligrams of sclareol per kilogram of fresh plant weight.

U.S. Pat. No. 4,988,527 describes the use of sclareolide for enhancing the organoleptic properties of food stuff whereby, for example, the sweetness of a jelly resulting from the use of a non-nutritive sweetener such as aspartame is enhanced by mixing sclareolide with the non-nutritive sweetener.

Test compounds in this invention can be individual compounds or mixtures of individual compounds or extracts of plants or fractionated extracts of plants or purified extracts of plants, any of which can be herein referred to as a test compound.

An objective of the assays used in this invention is to discover and identify or find and isolate compounds or mixtures of compounds that can be used to treat obesity. Adipocytes play a role in the storage of energy in the form of lipids, and serve as endocrine cells that regulate the breakdown and synthesis of lipids. Fully developed adipocytes synthesize and accumulate triglycerides, and produce high levels of the enzyme glycerol-3-phosphate dehydrogenase (GPDH). In addition, the breakdown of triglycerides (lipolysis) leads to the secretion of fatty acids and glycerol in the cell environment.

Fully developed adipocytes synthesize and accumulate triglycerides. The breakdown of triglycerides (i.e., lipolysis) leads to the secretion of fatty acids and glycerol in the cell environment. Compounds identified in this invention that stimulate lipolysis, i.e. the break down existing stored triacylglycerol, can be used to reduce the storage of fat in the body, and subsequently to reduce body weight. Additionally, lipolytic compounds may break down existing lipids/fat cells, or at least reduce the fat content of cells.

Compounds identified in the assays of this invention that block or inhibit adipogenesis (i.e., the differentiation of preadipocytes to adipocytes) are useful in preventing the development of cells whose function is the accumulation and/or synthesis of stored triacylglycerol/fat. As the adipocyte secretes a number of inflammatory cytokines, blocking the differentiation process would also result in an overall lack of inflammatory mediators such as TNF-α, whose presence is correlated with insulin resistance. Therefore, inhibitors of adipogenesis will prevent the accumulation of fat as well as reduce the insulin resistance associated with diabetes. We assess inhibition of adipogenesis using the following assay methods.

Method i): Oil Red O staining which stains fat droplets in fat cells and thereby gives a directly related indication of the level of adipogenesis as a function of the amount of staining of fat droplets.

Method ii): GPDH or glyceraldehyde phosphate dehydrogenase is a key enzyme involved in the pathway of triglyceride synthesis in the glycolytic pathway. Adipocytes express high levels of this enzyme. Therefore, a reduction in GPDH levels is indicative of inhibition of adipogenesis (prevention of fat accumulation in cells).

Method iii): Assay to observe de-differentiation of adipocytes to preadipocytes can be used to detect compounds and mixtures of compounds that are capable of breaking down existing stores of body fat. This assay identifies compounds and mixtures of compounds than induce the differentiation of adipocytes to preadipocytes and is quantitatively assessed by developing a color response using Oil Red O staining or by measuring GPDH levels as in methods i) and ii), respectively. Such compounds and mixtures of compounds as extracts of plants can have a direct effect on reducing weight because they cause fat cells to become non-fat cells (preadipocytes).

Method iv) Leptin Secretion assay can be used to determine the presence of leptin which is a product of the Ob gene. It is a hormone secreted by mature adipocytes that plays a role in regulating body fat storage. High levels of leptin circulating in the blood indicate hormonally that energy stores are high, and therefore mitigate the need for further food intake. Compounds or mixtures of compounds of this invention that increase leptin secretion can be administered orally to an overweight or obese person to reduce appetite in that person, and therefore to reduce food intake by that person.

The assays of this invention are described hereinbelow.

Assay 1. Lipolysis Assay.

A colorimetric assay is used to screen for compounds and mixtures of compounds that induce lipolysis or the breakdown of lipids.

In this assay, pre-adipocyte cells are seeded in 96-well plates and are induced to convert to adipocytes over the course of a 10–15 day treament with lipolytic reagents. After cells have converted to adipocytes, the cells are starved, and then subsequently treated with or exposed to test compounds or mixtures of compounds or extracts of plants or fractionated extracts of plants. The adipocytes are treated with test compounds in the presence of a surrounding cell medium. Over the course of 1 to 3 hours after exposure to the test compounds or mixture of compounds, the amount of glycerol present in the cell medium is measured. Glycerol and fatty acids are hydrolysis products of triglycerides, and glycerol is released from cells after enzymatic hydrolysis or breakdown of lipids.

Results are expressed as a percentage of the amount of glycerol present detected in a reference assay comprising an untreated control. Untreated controls are cells that are treated with vehicle only (such as 100% DMSO). A compound that is active in the mechanism of lipolysis of a triglyceride can exhibit at least 120% to 150% of the amount of glycerol released relative to an untreated control.

Assay 2. Inhibition of Adipocyte Differentiation.

Inhibition of adipocyte differentiation is assayed by measuring the levels of the enzyme glycerol-3-phosphate dehydrogenase (GPDH). GPDH is involved in the pathway of triglyceride synthesis in the glycolytic pathway. Colorimetric assays can be used to screen for compounds and mixtures of compounds than inhibit the differentiation of preadipocytes to adipocytes. Oil Red O is a colorimetric assay that can be used to stain lipids in adipocytes.

In this assay pre-adipocyte cells require 10 to 15 days to differentiate into adipocytes. Pre-adipocyte cells are seeded in 96-well plates and induced to convert to adipocytes over 10–15 days. On day 1 and every 3 days thereafter test compounds are added to the cells to determine the extent to which the compounds block the conversion of preadipocytes to adipocytes. After cells have undergone the 10–15 days required to differentiate, cells are assessed for GPDH activity.

Results are expressed as a percentage of the untreated control average. Untreated controls are cells that are treated with vehicle only (100% DMSO), and have high levels of GPDH activity (typical of adipocytes). Compounds that do block differentiation will cause cells to show little or no GPDH activity. A lead compound in the GPDH assay would exhibit a 40–50% or more decrease in GPDH expression when compared to the untreated controls.

For the Oil Red O assay, cells that do not take up the red dye have failed to convert to adipocytes. Compounds or mixtures of compounds evaluated in this assay are positive or good leads when cells do not take up red dye. Compounds that block differentiation of cells to adipocytes (fat cells) would be useful in that they would prevent cells from accumulating fat/lipids. In effect, fat would not be stored when cells have all the energy they require. These compounds can be used to treat obesity and over weight conditions.

Assay 3. De-Differentiation of Adipocytes to Preadipocytes.

This assay comprises a colorimetric assay to screen for compounds and mixtures of compounds that induce the differentiation of adipocytes to preadipocytes. The presence of such compounds is determined by measuring the relative levels of the enzyme GPDH. In this assay, pre-adipocyte cells are seeded in 96-well plates and induced to convert to adipocytes over the course of a 10–15 day treatment with lipolytic reagents. After cells have fully differentiated to adipocytes they are treated with compounds or mixtures of compounds to be screened over the next 10–15 days to convert the cells 'back' to preadipocytes and measure the efficacy of the compounds to de-differentiate the adipocytes back to preadipocytes. GPDH levels present in the cells are measured to determine if the cells still express the adipocyte phenotype. Results are expressed as GPDH levels present in the cells as a percentage of GPDH levels present in an untreated control average, the untreated control comprising adipocytes, i.e., adipocyte cells that are treated with vehicle only (100% DMSO). A compound useful in the treatment of conditions of overweight and obesity and related disorders would show GPDH levels 30–50% lower than untreated control in this assay, and would be useful as an anti-obesity reagent. Compounds or mixtures of compounds that induce lipolysis can be useful when administered to a body, preferably by an oral route, to reduce the storage of fat in the body. Additionally, such compounds and mixtures of compounds can be useful to break down existing lipids in fat cells and reduce the fat content of cells. Treatment of an overweight person or obese person can reduce that person's body mass index from levels identified as above normal to lower levels, preferably to levels in a normal range.

Assays useful to discover compounds and mixtures of compounds in this invention are described in the following.

Protocol for 96-Well Adipogenic Differentiation Assay (GPDH Assay)

L1 cell differentiation is obtained in a process comprising the following steps.
1) 5,000 to 10,000 cells per well of L1 cells are seeded in poly-D-lysine-treated plates containing an array of wells (e.g., 96 wells per plate) which are incubated at 30 to 37° C. in an atmosphere comprising carbon dioxide, oxygen, and nitrogen.
2) If the cells are 100% confluent 24 hours after seeding, the plates are incubated at the same conditions for an additional 48 hours;

2 days after confluent (three days after seeding) the cells are treated with MDI (i.e., MDI is Differentiation media causes the 3T3-L1 preadipocytes (fibroblast cells) to differentiate into adipocytes (fat cells). Differentiation media is composed of:

Per 100 ml of differentiation media
90 mL DMEM media
10 mLFCS
1% pen/strep
1 ml methylisobutylxanthine (stock 11.5 mg/mL)
100 ul dexamethasone (stock 0.4 mg/mL)
1 ml insulin (stock 1 mg/mL)
3) ) and add TNF-alpha (5, 10 ng/ml) to wells used as control wells with MDI;
4) 2 days later the media is removed and replaced with fresh media+units of insulin;
5) 3 days later the media is removed and replaced with media+¼ of the amount of insulin used in the previous step;
6) 2 days later the media is removed and replaced with media only; wherein
7) the cells are fully differentiated 3 days later (after total of 11 days post MDI treatment).

The following are used as controls.

A negative control comprises addition of 10 µl of TNF-alpha at a concentration of 5 ng/ml which is added to at least one of the wells as a control on the same day as MDI treatment.

Positive Control: MDI Treatment

GPDH Assay

Cells to be assayed are prepared for GPDH assay in a process comprising the following steps.
1) Wash cells in each well once (1×) with PBS (phosphate buffered saline that is free of calcium and magnesium);
2) Add ice-cold homogenization solution to each well using 100 ul of solution per well
3) Store plates at −20 C. to break up the cells and release GPDH.

The GPDH assay comprises an enzyme reaction in a process comprising the following steps.
add 90 uL (microliters) of enzyme reaction mix comprising Enzyme Reaction Mix composition:
0.1 M triethanolamine
2.5 mM EDTA
0.1 mM Beta-mercaptoethanol
334 uM NADH
pH 7.7 (using HCl)

1) to each well and pre-incubate for 10 minutes at 37° C.;
2) add 10 ul (microliters) of DHAP which is defined as Dihydroxyacetone phosphate (at a concentration of 4 mM of stock solution in $H_2O$) to start the assay;
3) measure absorbance in each well at 340 nm for 4–5 minutes Controls comprise the following separate control wells in which absorbance at 340 nm is also measured for 4–5 minutes:
    1 well w\o (without) NADH, but which receives PBS buffer only
    at least one well used with No MDI treatment
    at least one well used with TNF-alpha treatment
    at least one well used with MDI treatment only with vehicle addition;
    at least one well used with MDI treatment only without vehicle addition.

A homogenization solution is prepared comprising the following ingredients and pH:
20 mM Tris
1 mM EDTA
1 mM Beta-mercaptoethanol
pH 7.3

An enzyme reaction mixture is prepared comprising the following ingredients and pH:
0.1 M triethanolamine
2.5 mM EDTA
0.1 mM Beta-mercaptoethanol (optionally using DTT or 1,4-Dithio-DL-threitol instead of beta-mercaptoethanol)
334 uM NADH
pH 7.7 (using HCl)

A useful protocol for the de-differentiation assay in this invention comprises the following steps.

L1 cell differentiation
1) Seed 5–10K/well of Li cells in poly D lysine treated plates
2) 100% confluent next day. Continue to incubate for 2 more days
3) 2 days after confluent treat with MDI
    add TNFalpha with MDI
    add compounds to be tested at this time as well
4) 2 days later remove media and add media+insulin
5) 3 days later remove media and add media+¼ insulin
6) 2 days later and media only
7) cells fully differentiated 3 days later (after total of 11 days post MDI treatment) controls:
Negative: TNFalpha (5 ng/ml)
    added to wells on the same day as MDI treatment
Positive Control: MDI treatment
Induce Cells to revert back to preadipocytes
1) administer TNF-alpha to induce reversion back to preadipocytes GPDH Assay
1) carry out same as previously, but this time measuring a "lack" of GPDH activity as anindication of blockage of lipogenesis.

The invention is further described by reference to the figures.

FIG. 1A shows the effect of sclareol on lipolysis in 12-day old differentiated adipocytes. Cells were treated with 5 or 50 ug/ml of sclareol for 3 hours. Conditioned media was then collected and assessed for glycerol release using GPO trinder assay (Sigma). Results are expressed as a percentage of the untreated control average. Untreated controls are cells that are treated with vehicle only. Results are presented as the mean +/– SD of three replicated experiments.

Figure 1B:
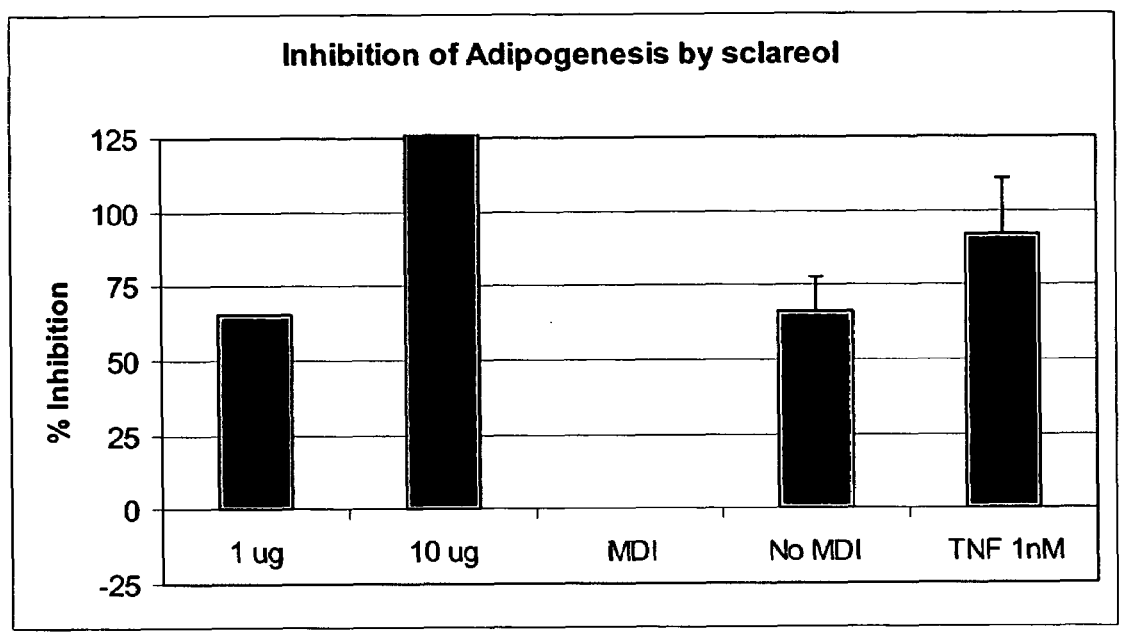
FIG. 1B shows the effect, after 12 days in terms of measured GPDH levels, of sclareol on adipogenesis in 3T3-L1 cells that were differentiated into adipocytes. Results are expressed as percent inhibition compared to a positive control average shown as 0% inhibition.

FIG. 1B shows the effect of sclareol on adipogenesis. 3T3-L1 cells were treated with 5 or 50 ug/ml of PPC1 three times during the course of differentiation into adipocytes. After 12 days, GPDH levels were measured. Results are expressed as percent inhibition compared to the positive control average (positive control is shown here as 0% inhibition). Results are presented as the mean +/– SD of three replicated experiments.

Figure 2A:
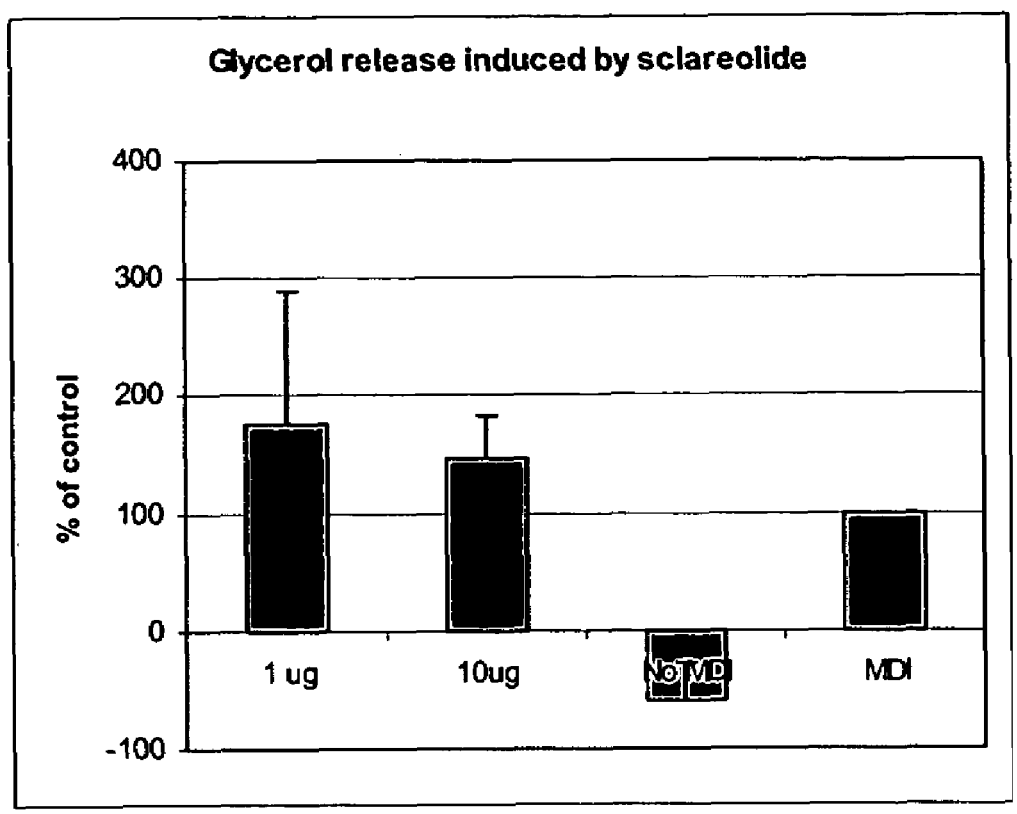
FIG. 2A shows the effect, as a percentage of the untreated control average, of sclareolide on lipolysis via glycerol release in 12-day old differentiated adipocytes treated with 5 or 50 ug/ml of sclareolide for 3 hours.

FIG. 2A shows the effect of sclareolide on lipolysis in 12-day old differentiated adipocytes. Cells were treated with 5 or 50 ug/ml of sclareolide for 3 hours. Conditioned media was then collected and assessed for glycerol release using GPO trinder assay (Sigma). Results are expressed as a percentage of the untreated control average. Untreated controls are cells that are treated with vehicle only. Results are presented as the mean +/– SD of three replicated experiments.

Figure 2B:
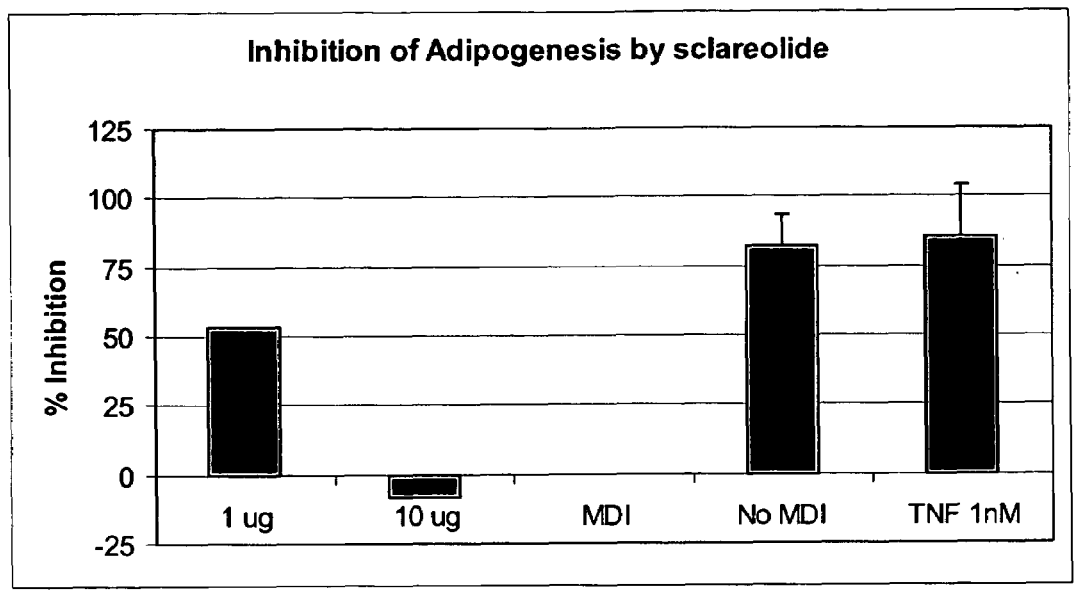
FIG. 2B shows the effect, after 12 days in terms of measured GPDH levels, of sclareolide on adipogenesis in 3T3-L1 cells that were differentiated into adipocytes. Results are expressed as percent inhibition compared to a positive control average shown as 0% inhibition.

FIG. 2B shows the effect of sclareolide on adipogenesis. 3T3-L1 cells were treated with 5 or 50 ug/ml of sclareolide three times during the course of differentiation into adipocytes. After 12 days, GPDH levels were measured. Results are expressed as percent inhibition compared to the positive control average (positive control is shown here as 0% inhibition). Results are presented as the mean +/– SD of three replicated experiments.

FIG. 3 shows the results of a fractionation by HPLC of fractions isolated and collected at 30 second or 1 minute HPLC eluant flow time intervals of two plant extracts designated as PM765 and as PM902 that are active in the adipocyte differentiation blocking assay.

FIG. 4 is a schematic representation of a commercially available ELISA assay that can be used to detect compounds that induce the release of leptin in this invention.

Figure 5:
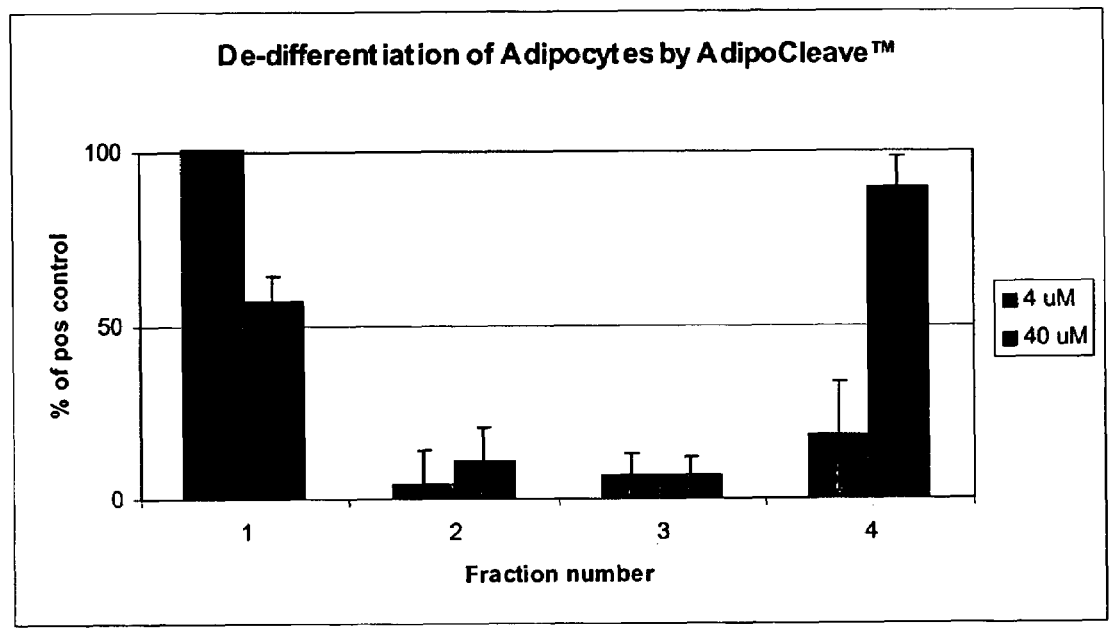
FIG. 5 is a bar graph showing de-differentiation of Adipocytes by AdipoCleave™.

FIG. 5 is a bar graph showing de-differentiation of Adipocytes by AdipoCleave™. More particularly, 3T3-L1 pre-adipocytes were induced to differentiate into adipocytes in a 96-well plate for 12 days. Adipocytes were then treated with Adipo-Cleave™ (fractions #1–4) at a concentration of 4γM three times over the course of the next 10 days. Cells were then screened for the adipocyte marker, 6PDH. Results are expressed in FIG. 5 as a percentage of the positive control (100%).

Figure 6:
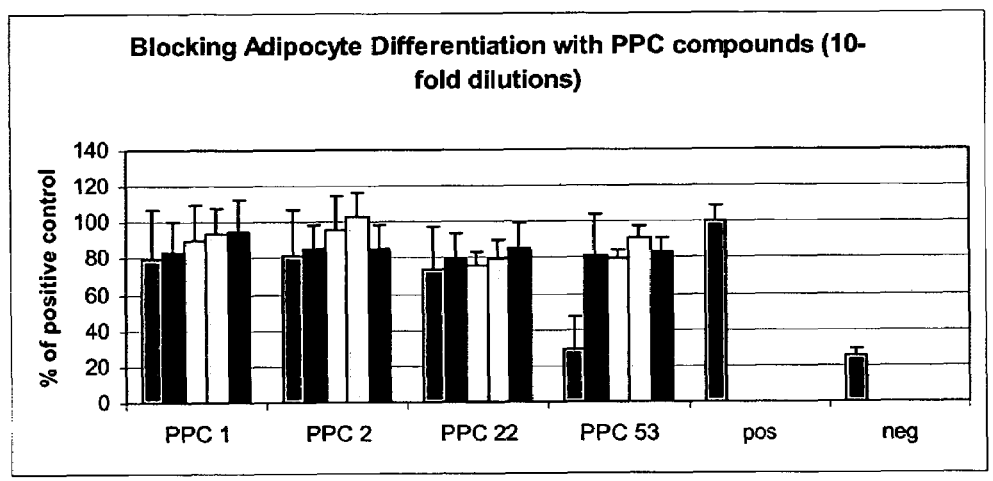
FIG. 6 is a bar graph showing the blocking of adipocyte differentiation, as a percent of positive control, by representative compounds designated as "PPC compounds" after 10-fold dilution, wherein PPC 1 is sclareol and PPC 2 is sclareolide.

FIG. 6 is a bar graph showing the blocking of adipocyte differentiation, as a percent of positive control, by representative compounds designated as "PPC compounds" after 10-fold dilution, wherein PPC 1 is sclareol and PPC 2 is sclareolide.

Compositions comprising compounds or mixtures of compounds or extracts of plants can be assayed by the above methods and identified to be useful in the treatment of over weight conditions and obesity and related disorders.

Compositions that are active in the assays of this invention can be formulated with pharmaceutically acceptable or nutraceutically acceptable excipients and ingredients to form oral dosage forms. Suitable oral dosage forms include liquid solutions such as a solution comprising a vegetable- and/or animal- and/or fish-derived oil, optionally also containing at least one pharmaceutically acceptable surface active agent, optionally also containing a low molecular weight hydroxy compound such as ethanol and/or glycerol, and the solution enclosed in a soft gelatin capsule for oral administration. The active component can be present in amounts from about 0.1% to about 50% of the solution, preferably from about 2% to about 40% of the solution, and more preferably from about 5% to about 30% of the solution. Solid compounds of this invention can also be formulated into tablets and capsule for oral administration or used as powders for addition to foodstuff prior to consumption by a patient. Coloring and flavoring ingredients acceptable for food or pharmaceutical use can be used in such formulations.

Compositions that are active in the assays of this invention include sclareol and sclareolide as well as sclareol-like or sclareolide-like compounds and plant extracts containing these compounds.

A method of treatment of obesity in a patient with a body mass index of 30 kg/m$^2$ or greater comprises administration to the patient of sclareol or sclareolide.

A method of treatment of an overweight condition in a patient comprises administration to the patient of sclareol or sclareolide, wherein the body mass index of the patient is reduced from the range of about 30 kg/m$^2$ to about 25 kg/m$^2$, to about 24 kg/m$^2$.

A method of treatment of obesity in a patient comprises administration to the patient of sclareol or sclareolide, wherein the body mass index of the patient is reduced from a value greater than 30 kg/m$^2$ to a value of 30 kg/m$^2$ or less.

A process for the identification of a composition or compound useful in the treatment of an overweight or obese person, comprises an assay comprising:

a) obtaining an extract of an ethnobotanical plant, and evaluating the activity of the extract in an assay selected from the group consisting of a lipolysis assay, an assay that measures the amount of glycerol introduced by a cell into a suspension medium of the cell, an adipocyte differentiation assay, an assay that measures the level of the enzyme glycerol-3-phosphate dehydrogenase, an assay that measures the inhibition of differentiation of preadipocytes to adipocytes, an assay that measures the accumulation of lipid in an adipocyte, an assay that measures the de-differentiation of adipocytes into preadipocytes, and combinations thereof.

What is claimed:

1. A method of treatment of obesity in a patient with a body mass index of 30 kg/m$^2$ or greater, comprising administering a therapeutically effective amount of at least one of sclareol and sclareolide to the patient to reduce said body mass index.

2. The method of treatment as in claim 1, comprising administering to the patient of at least one of a compound of sclareol and sclareolide in an amount effective to reduce the body mass index of the patient from a value greater than 30 kg/m$^2$ to a value of 30 kg/m$^2$ or less.

3. The method of treatment as in claim 1, wherein said at least one of a compound of sclareol and sclareolide is substituted with one of alkalyl, aryl, halogen, hydroxyl and amino groups.

4. The method of treatment as in claim 1, wherein said at least one of a compound of sclareol and sclareolide comprises at least one of an optical isomer, chiral compound and a mixture of optical isomer and chiral compound thereof.

5. The method of treatment as in claim 1, further comprising administering said compound as an amount effective to at least one of induce lipolysis and increase leptin secretion.

6. The method of treatment of claim 1, wherein said compounds are obtained as an extract of a plant.

7. The method of claim 1, further comprising administering said compound in oral form.

* * * * *